(12) United States Patent
DePaula et al.

(10) Patent No.: US 8,351,770 B2
(45) Date of Patent: Jan. 8, 2013

(54) IMAGING STATION AND METHOD FOR REPEATABLE ALIGNMENT OF IMAGES

(75) Inventors: Lawrence C. DePaula, Tucson, AZ (US); Karleen G. Seybold, Tucson, AZ (US); Frederick C. Mertz, San Diego, CA (US); Robert K. Pina, Ramona, CA (US); Ivans S. Chou, Chula Vista, CA (US); Clara Curiel, Tucson, AZ (US)

(73) Assignees: Raytheon Company, Waltham, MA (US); Arizona Board of Regents on Behalf of the University of Arizona, Tucson, AZ (US)

( * ) Notice: Subject to any disclaimer, the term of this patent is extended or adjusted under 35 U.S.C. 154(b) by 756 days.

(21) Appl. No.: 12/404,864

(22) Filed: Mar. 16, 2009

(65) Prior Publication Data

US 2010/0232773 A1    Sep. 16, 2010

(51) Int. Cl.
*G03B 29/00* (2006.01)
(52) U.S. Cl. .......................................... 396/14
(58) Field of Classification Search ................ 396/5, 14; 348/77; 116/213
See application file for complete search history.

(56) References Cited

U.S. PATENT DOCUMENTS

| | | | |
|---|---|---|---|
| 3,776,614 A * | 12/1973 | Kloots et al. ................ | 359/376 |
| 5,117,283 A * | 5/1992 | Kroos et al. ................ | 348/564 |
| 5,386,447 A | 1/1995 | Siczek | |
| 6,141,034 A | 10/2000 | McCutchen | |
| 6,288,703 B1 * | 9/2001 | Berman et al. ................ | 345/600 |
| 7,050,085 B1 | 5/2006 | Park et al. | |
| 2002/0024517 A1 | 2/2002 | Yamaguchi et al. | |
| 2004/0057608 A1 | 3/2004 | Souluer | |
| 2005/0090734 A1 | 4/2005 | Contrada et al. | |
| 2007/0270690 A1 | 11/2007 | Woerlein | |
| 2007/0282228 A1 | 12/2007 | Einav et al. | |
| 2008/0077005 A1 * | 3/2008 | Piron et al. ................ | 600/411 |
| 2008/0114270 A1 | 5/2008 | DiSilvestro et al. | |
| 2008/0125630 A1 * | 5/2008 | Caylor ................ | 600/300 |

FOREIGN PATENT DOCUMENTS

WO    WO-2010107467 A1    9/2010

OTHER PUBLICATIONS

Halpern, A. C., et al., "Standardized positioning of patients (poses) for whole body cutaneous photography", *J Am Acad Dermatol.*, 49(4), (Oct. 2003), 593-8.

(Continued)

*Primary Examiner* — Rochelle-Ann J Blackman
*Assistant Examiner* — Linda B Smith
(74) *Attorney, Agent, or Firm* — Schwegman Lundberg & Woessner, P.A.

(57) ABSTRACT

Embodiments of an imaging station and method for repeatable alignment of images are generally described herein. In some embodiments, the imaging station includes a rotatable stage and a monostand. The rotatable stage may include a structure to support sets of handles for positioning of a subject's hands for at least some of the body poses. A camera is positioned on the monostand for capturing images of the subject and is configured to allow the camera to be repeatably positioned with respect to the rotatable stage for each body pose.

19 Claims, 10 Drawing Sheets

OTHER PUBLICATIONS

Roning, J., "Registration of nevi in successive skin images for early detection of melanoma", *Fourteenth International Conference on Pattern Recognition, 1998. Proceedings. IEEE*, vol. 1, (352-357), Aug. 1998.

"Internationai Application Serial No. PCT/US2010/000583, Search Report mailed May 14, 2010", 4 pgs.

"International Application Serial No. PCT/US2010/00583, Written Opinion mailed May 14, 2010", 9 pgs.

"International Application Serial No. PCT/US2010/000583, International Preliminary Report on Patentability mailed Sep. 29, 2011", 8 pgs.

* cited by examiner

FIG. 4 BODY POSES

US 8,351,770 B2

IMAGING STATION AND METHOD FOR REPEATABLE ALIGNMENT OF IMAGES

CROSS-REFERENCE TO RELATED APPLICATIONS

This patent application relates to U.S. patent applications Ser. No. 12/133,163 entitled "IMAGE PROCESSING SYSTEM AND METHODS FOR ALIGNING SKIN FEATURES FOR EARLY SKIN CANCER DETECTION SYSTEMS" filed Jun. 4, 2008, and Ser. No. 12/147,081 entitled "GRAPHICAL USER INTERFACE (GUI), DISPLAY MODULE AND METHODS FOR DISPLAYING AND COMPARING SKIN FEATURES" filed Jun. 26, 2008.

TECHNICAL FIELD

Embodiments pertain to imaging stations and methods for imaging. Some embodiments pertain to body imaging for skin cancer detection.

BACKGROUND

Skin cancer is an increasing health problem with many new cases diagnosed each year. Early detection of skin cancer may result in a significantly greater chance of recovery and reduction in health-care resource expenditures. One difficulty with early skin cancer detection is that there is no objective method for skin cancer screening available for use in a clinical setting. Conventionally, skin cancer screening is performed by combining visual observations with manual handwritten tracking methods done locally in a physician's office. Even when images of skin-features are used, it remains difficult to accurately and repeatably compare images taken over time, particularly because skin features are difficult to align. Aligning and comparing those images in a reliable and clinically useful way is not currently available.

Thus, there are general needs for systems and methods that can capture images in a precise and repeatable manner. There are also general needs for imaging stations and methods for repeatable alignment of images suitable for use in skin-cancer detection.

DETAILED DESCRIPTION

The following description and the drawings sufficiently illustrate specific embodiments to enable those skilled in the art to practice them. Other embodiments may incorporate structural, logical, electrical, process, and other changes. Examples merely typify possible variations.

Figure 1:
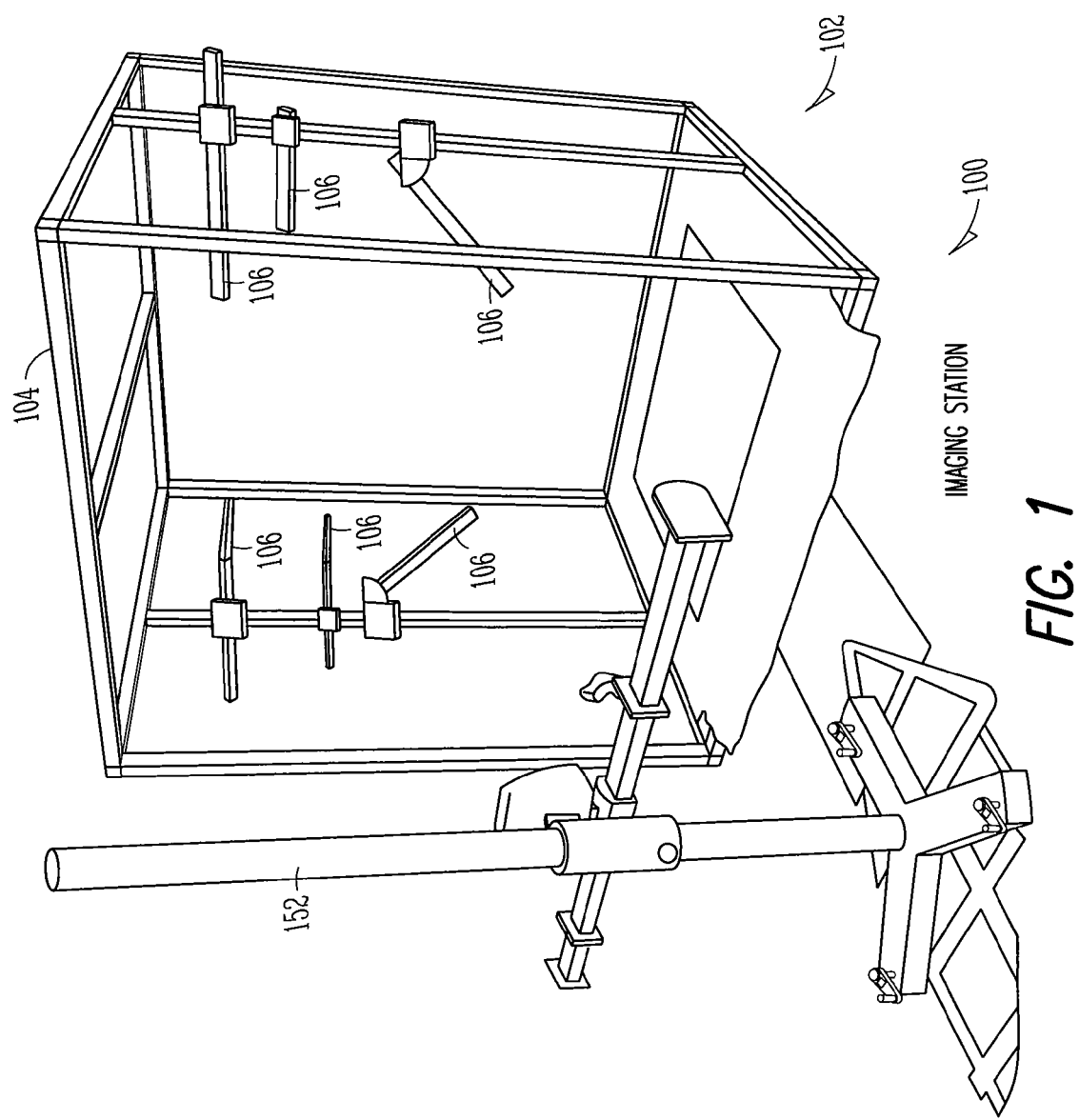
FIG. 1 is a perspective view of an imaging station, in accordance with some embodiments.

FIG. 1 is a perspective view of an imaging station, in accordance with some embodiments. Imaging station 100 may provide for precise and repeatable alignment of images taken over time and may comprise a stage 102 and a monostand 152. The stage 102 may have a structure 104 to support sets of handles 106 for positioning a subject's hands for at least some of the body poses. The monostand 152 is configured for placement of a camera for capturing images of the subject and is configurable to allow the camera to be repeatably positioned in different positions with respect to the stage 102 for the body poses. In some embodiments, the stage 102 may be a rotatable stage.

Figure 2A:
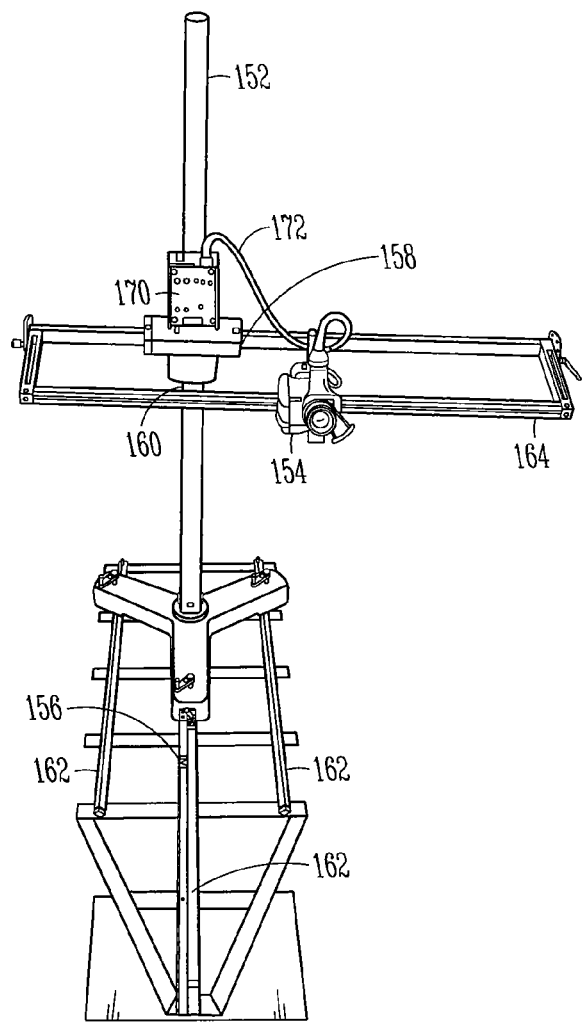
FIG. 2A illustrates a monostand of the imaging station, in accordance with some embodiments.

FIG. 2A illustrates the monostand 152 of the imaging station 100 (FIG. 1), in accordance with some embodiments. Monostand 152 may be configured for placement of a camera 154 thereon for capturing images of a subject and may include elements to allow the camera 154 to be repeatably positioned with respect to the stage 102 for each body pose. In some embodiments, the monostand 152 includes forward-backward (z-direction) camera position-indicating element 156, a left-right (x-direction) camera position-indicating element 158, and up-down (y-direction) camera position-indicating element 160. Forward-backward camera position-indicating element 156 may indicate the distance from the camera 154 to the stage 102. Left-right camera position-indicating element 158 may indicate a left-right position of the camera 154 with respect to the monostand 152. Up-down camera position-indicating element 160 may indicate an up-down position of the camera 154 with respect to the floor of the stage 102. These position-indicating elements allow the three-dimensional position of the camera 154 with respect to a subject on the stage 102 to be determined and recorded for each body pose, and to be accurately repeated at later times for each body pose. In some embodiments, forward-backward camera position-indicating element 156 may indicate the distance from the camera 154 or the monostand 152 to a center axis of rotation of stage 102. In some embodiments, camera position-indicating elements 156, 158 and 160 may comprise measuring tapes.

As illustrated in FIG. 2A, the monostand 152 includes support element 164 to support the camera 154. The left-right position-indicating element 158 is provided on the support element 164. In some embodiments, support element 164 is configured to slide horizontally to allow the left-right position of the camera 154 to be changed. In some embodiments, the camera 154 may also be configured to be rotated ninety degrees for certain body poses.

In accordance with these embodiments, the camera 154 may be moved up and down, side-to-side and rotated for capturing images of the different body poses. For example, the camera 154 may be placed lower to capture images of a subject's lower legs, may be placed mid-height for mid-body images, and may be placed higher up for upper-body images.

Camera 154 may, for example, be rotated ninety-degrees for vertical compositions. The monostand 152 may be moved back and forth to allow the camera to be positioned closer or further from the subject. As further illustrated in FIG. 2A, the monostand 152 may include tracks 162 to allow the monostand 152 to be positioned closer or further from the stage 102 (FIG. 1).

The camera 154 may be a high-resolution camera or image capture device. For example, the camera 154 may be a high-resolution digital camera with at least a thirty mega-pixel resolution. The resolution of the camera 154 may be selected based, at least in part, on the size of the particular skin-features to be aligned and mapped, the change in size of the particular skin-features to be identified, and/or the skin-feature alignment and registration algorithms that may be subsequently used to align corresponding skin features. Unlike some conventional imaging systems, camera 154 and imaging station 100 may be configured to capture images of large portions of the human body with many skin features. The high-resolution of camera 154 may allow the alignment and mapping of corresponding skin features on the order of one millimeter or less.

In some embodiments, a background of a predetermined color may be provided behind stage 102 opposite of the camera 154. The predetermined background color may be blue or a shade of blue, such as photo-blue or savage golf blue, although the scope of the embodiments is not limited in this respect. The use of a predetermined background color may allow for the separation of body pixels from background pixels in the image alignment process discussed below.

In some embodiments, the monostand 152 may include light source 170 and fiber-optic cable 172. The fiber-optic cable 172 may be coupled to the camera 154 to project light through a lens for use in focusing and framing images, although the scope of the embodiments is not limited in this respect.

Some of the more important risk factors with skin cancer detection are moles in persistently changing size and color and the presence of a large number of moles of at least a certain diameter. Embodiments of imaging station 100 allow for body images to be captured in a precise and repeatable manner. This provides for repeatable alignment and comparison of images suitable for use in skin-cancer detection. Accordingly, images of skin features, such as moles, taken over time (e.g., over periods of up to a year or two or more) may be easily aligned and compared.

Figure 2B:
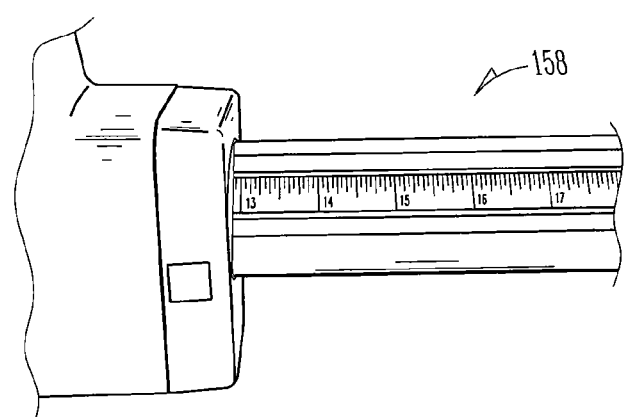
FIG. 2B illustrates a left-right camera position-indicating element of the monostand, in accordance with some embodiments.

FIG. 2B illustrates the left-right camera position-indicating element 158 of the monostand 152, in accordance with some embodiments. The left-right camera position-indicating element 158 may indicate a left-right position of the camera 154 (FIG. 2A) with respect to the center of the monostand 152. The left-right camera position-indicating element 158 allows the left-right position of the camera 154 to be recorded for each body pose, and repeated for corresponding body poses taken at a later time.

Figure 2C:
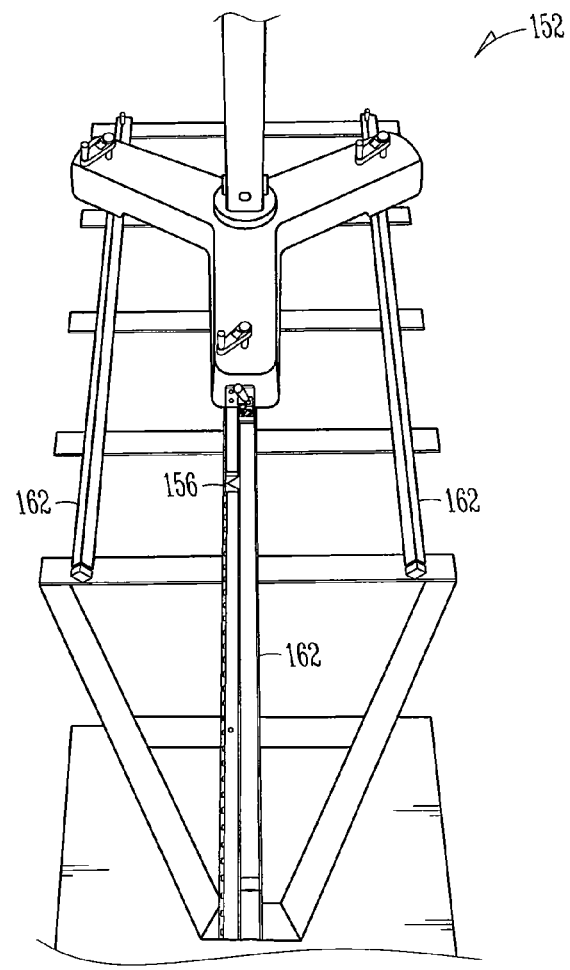
FIG. 2C illustrates tracks for movement of the monostand, in accordance with some embodiments.

FIG. 2C illustrates tracks 162 for movement of the monostand 152, in accordance with some embodiments. The tracks 162 to allow the monostand 152 to be positioned closer or further from stage 102 (FIG. 1). FIG. 2C also illustrates forward-backward camera position-indicating element 156 which may indicate a distance from the camera 154 to the stage 102 (FIG. 1). In some embodiments, the monostand 152 includes wheels (not illustrated) configured to ride in the tracks 162 to allow the monostand 152 to be positioned closer or further from stage 102 (FIG. 1).

Figure 2D:
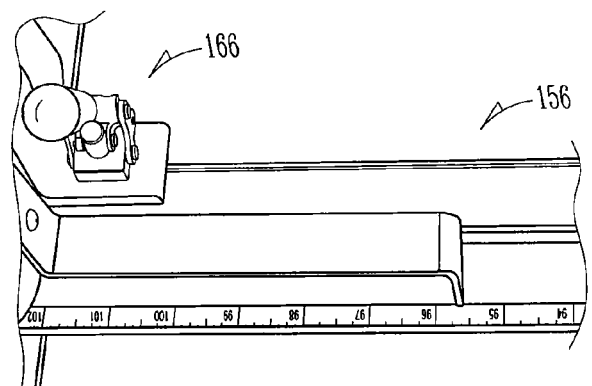
FIG. 2D illustrates a forward-backward position-indicating element of the monostand, in accordance with some embodiments.

FIG. 2D illustrates the forward-backward camera position-indicating element 156 of the monostand 152 (FIG. 2C), in accordance with some embodiments. In some embodiments, the monostand 152 may include locking element 166 to lock the monostand 152 on tracks 162 in a proper position for a body pose. The forward-backward camera position-indicating element 156 allows the forward-backward position of the camera 154 to be recorded for each body pose, and repeated for corresponding body poses taken at a later time.

Figure 3:
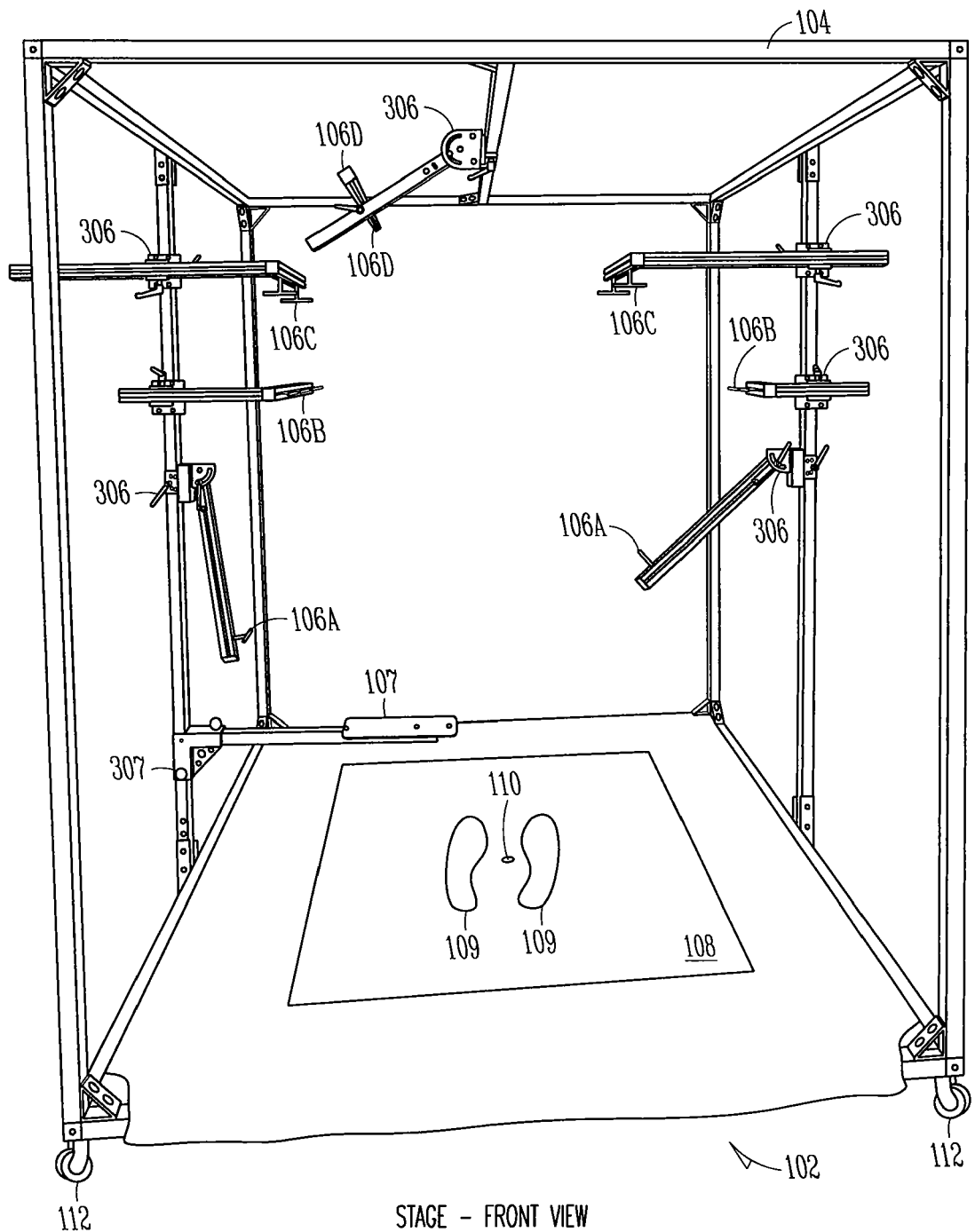
FIG. 3 illustrates a front view of a rotatable stage of the imaging station, in accordance with some embodiments.

FIG. 3 illustrates a front view of the stage 102 of the imaging station 100 (FIG. 1), in accordance with some embodiments. Stage 102 includes structure 104 to support sets of handles 106A-106D for positioning of a subject's hands for at least some of the body poses. Stage 102 may also include mat 108 with feet-position indicators 109 thereon. Stage 102 may also include foot platform 107 coupled to the structure 104 to support a foot of the subject for some of the body poses. In these embodiments, the feet-position indicators 109 may be provided around a central axis 110 so that the subject's position and the stage 102 may be rotated about the central axis 110. Although only one set of feet-position indicators 109 are illustrated, several sets of feet-position indicators 109 may be provided and used for different body poses. The feet-position indicators 109 may provide templates for positioning a subject's feet during some of the body poses.

Each of the handles 106A-106D may be associated with a handle-position indicator 306 to indicate a position of the associated handle 106 to allow the associated handle to be repeatably positioned for a particular body pose. Foot platform 107 may be associated with foot platform position indicator 307 to indicate a position of the foot platform 107. The foot platform position indicator 307 may allow foot platform 107 to be repeatably positioned for a particular body pose. Furthermore, the use of foot platform 107 may allow for its height to be set based on the subject's height or leg length. In accordance with embodiments, for each body pose, either one or more handles 106A-106D are grasped and/or the foot platform 107 is used. The position of the handles 106A-106D and/or foot platform 107 as indicated on the associated position indicators are recorded for a particular body pose so that the same positions may be repeated a subsequent times for corresponding body poses.

Stage 102 is configured to rotate around the central axis 110 with respect to the monostand. In some embodiments, stage 102 is configured to rotate to one of four ninety-degree positions with respect to the monostand. In this way, images may be captured on each side of the subject, thereby minimizing movement of the subject while providing increased repeatability of image alignment. In some embodiments, the stage 102 may include wheels 112 to allow the structure 104 to be rotated. Wheels 112 may be provided at the corners of structure 104 as shown, although this is not a requirement. In some alternate embodiments, the monostand 152 may be configured to be positioned on each side of the stage 102 or may be configured to rotate around the stage 102.

In some other embodiments, system 100 may include a non-rotatable stage similar to stage 102. In these embodiments, a monostand, such as the monostand 152, may be provided in each of the four ninety-degree positions around stage 102.

Figure 4:
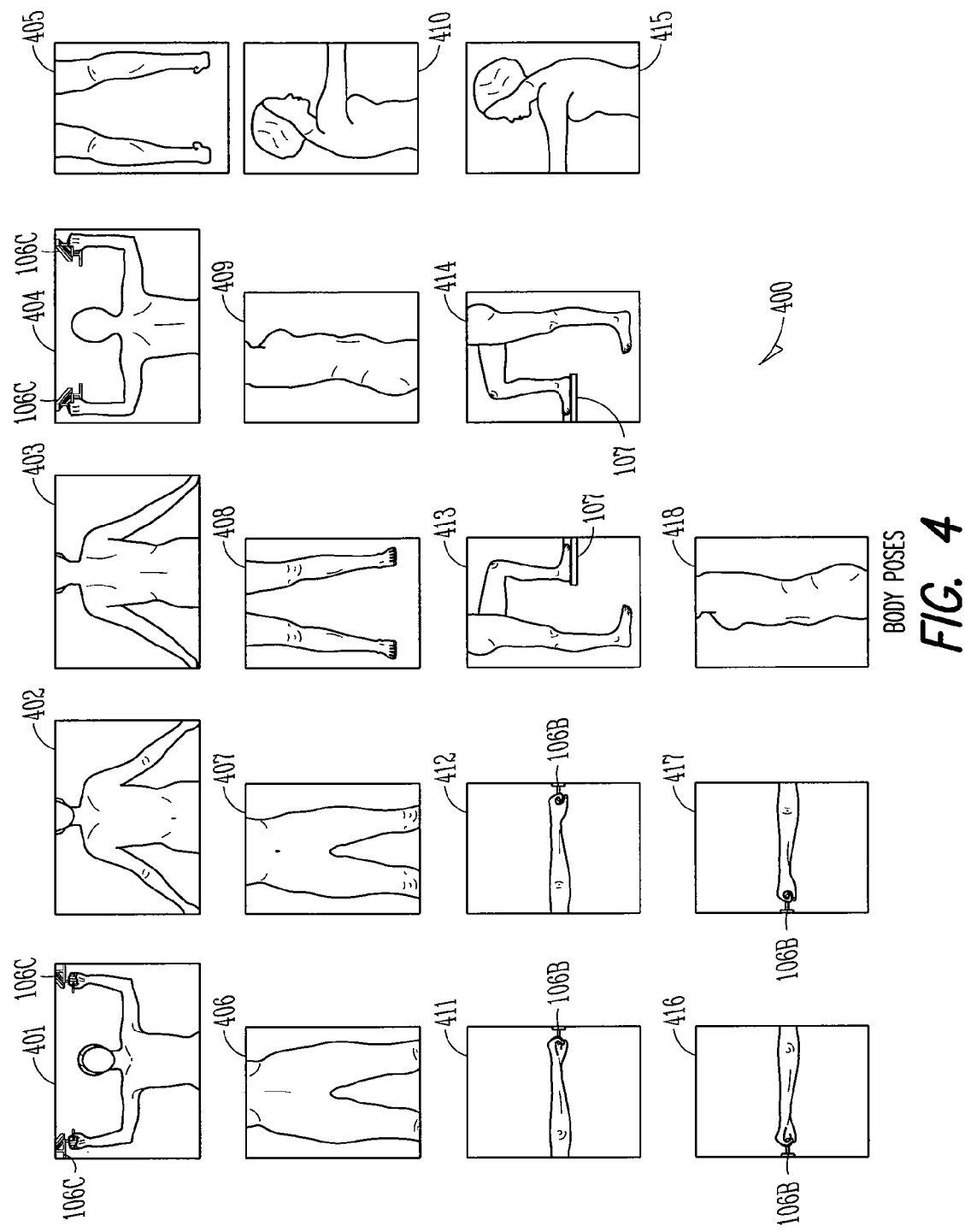
FIG. 4 illustrates a set of body poses, in accordance with some embodiments.

FIG. 4 illustrates a set of body poses, in accordance with some embodiments. Set of body poses 400 may include: Upper Body Front body pose 401, Middle Body Front body pose 402, Middle Body Rear body pose 403, Upper Body Rear body pose 404, Lower Body Rear body pose 405, Middle Body Rear body pose 406, Middle Body Front body pose 407, Lower Body Front body pose 408, Middle Body Lateral Right body pose 409, Upper Body Lateral Right body pose 410, Lateral Right Arm body pose 411, Medial Left Arm body pose 412, Lower Body Right with Left Leg Raised body pose 413, Lower Body Left with Right Leg Raised body pose 414, Upper Body Lateral Left body pose 415, Lateral Left Arm body pose 416, Medial Right Arm 417, and Middle Body Lateral Left body pose 418.

In addition to the body poses illustrated in FIG. 4, additional images that may be captured include images of both sides of a subject's hands, images of both sides of a subject's feet, images of all sides of a subject's head including a top view, and images of a subject's shoulders (from the top). In some embodiments, a separate imaging station may be used to capture these additional images, although the scope of the embodiments is not limited in this respect.

The body poses illustrated in FIG. 4 provide for substantially complete imaging of the human body, although a greater number or a lesser number of body poses may be used. For each body pose, either one or more handles 106A (not shown in FIG. 4) 106C or 106B may be grasped by the subject and/or one of the subject's feet is placed on the foot platform 107. Note that only some of the body poses illustrated in FIG. 4 show the grasping of handles (e.g., body poses 401, 404, 411, 412, 416 and 417). In some embodiments, body poses 401-418 may be captured in the sequence illustrated in FIG. 4, although this is not a requirement. The sequence of body poses 401-418 illustrated in FIG. 4 may provide for increased subject comfort (e.g., less movement of the subject at the expense of increased movement of the camera 154 and/or the stage 102). Accordingly, embodiments provide a standardized image collection method allowing images of corresponding body images to be aligned in a precise and repeatable manner.

Figure 5:
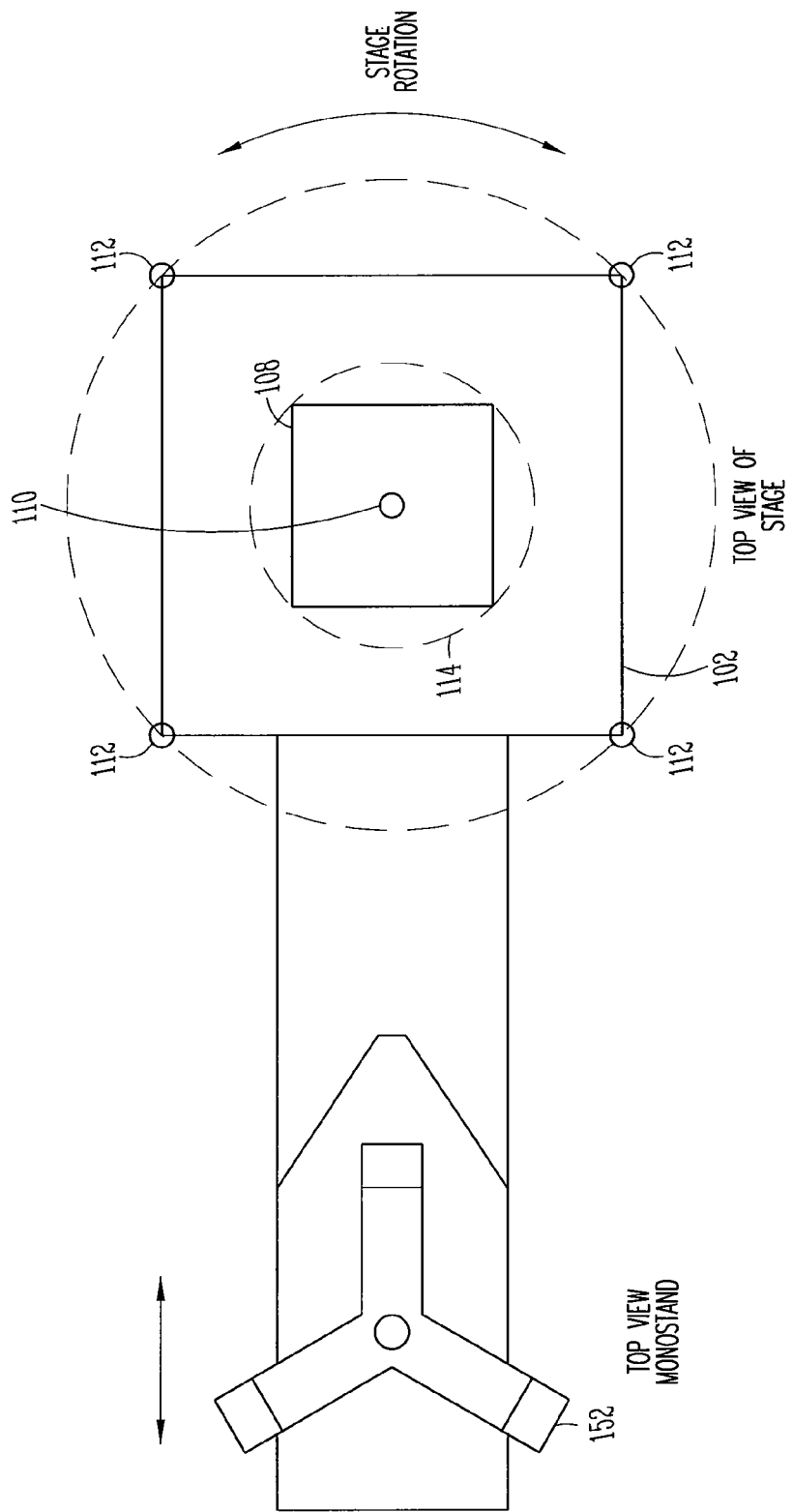
FIG. 5 illustrates a simplified top view of the monostand and rotatable stage, in accordance with some embodiments.

FIG. 5 illustrates a simplified top view of the monostand 152 and the stage 102, in accordance with some embodiments. As illustrated in FIG. 5, the stage 102 is configured to rotate around the central axis 110 using wheels 112. FIG. 5 also illustrates that the monostand 152 is configured to be positioned either closer or further from the stage 102. In some embodiments, the stage 102 may include a circular track 114 to provide for rotation of the stage 102 around the central axis 110. In these embodiments, the circular track 114 may be below the stage's platform and may include a set of ball bearings to operate like a 'lazy Susan'. Circular track 114 is illustrated below mat 108.

Referring to FIGS. 1-5, in some embodiments, imaging station 100 may be configured to allow data for each body pose to be recorded. The data for each body pose may include a body pose name or description, camera settings, camera position information as indicated by camera position-indicating elements of the monostand 152, a rotational position of the stage 102, and position indications of the handles that are grasped. For body poses that use a foot platform, the data may include a position indication for the foot platform. When a subsequent set of images for a subject are to be captured after an initial set of images are captured, imaging station 100 is configurable to allow the precise repeat capturing of an image for each of the body poses based on the data previously recorded for each body pose. Accordingly, through the use of the camera settings, the camera position information as indicated by camera position-indicating elements of the monostand 152, the rotational position of the stage 102, the indications of the handles 106 that are grasped and associated handle positions, and/or a position indication for the foot platform 107, repeatable and precise alignment of images may be achieved.

In some embodiments, imaging station 100 may be used to capture images as part of a skin-feature change-detection system, such as the skin-feature change-detection system disclosed in U.S. patent application Ser. No. 12/133,163. In these embodiments, imaging system 100 may be used to capture a body image and the skin-feature change-detection system may align skin features with a reference image that was taken at a different time. The skin-feature change-detection system may be used to identify changes in the skin features between the images and to display the changes for analysis by a physician, although the scope of the embodiments is not limited in this respect. The skin-feature change-detection system may include an image processing and feature alignment system to align skin features of a captured image with features of a reference image to generate a registered image from the captured image. The registered image may have its skin features aligned with corresponding skin features of the reference image. In some embodiments, the image processing and feature alignment system may utilize a pixel-to-pixel spatial coordinate transformation map for warping coordinates of a captured image to generate a registered image as an output. The skin-feature change-detection system may also include a skin-feature change-detection system to generate change-detection reports which may be based on a comparison of the aligned skin features of the registered image and the reference image. The change-detection reports may identify skin features, such as nevi, that have changed based on predetermined criteria between the reference image and the registered image.

Figure 6:
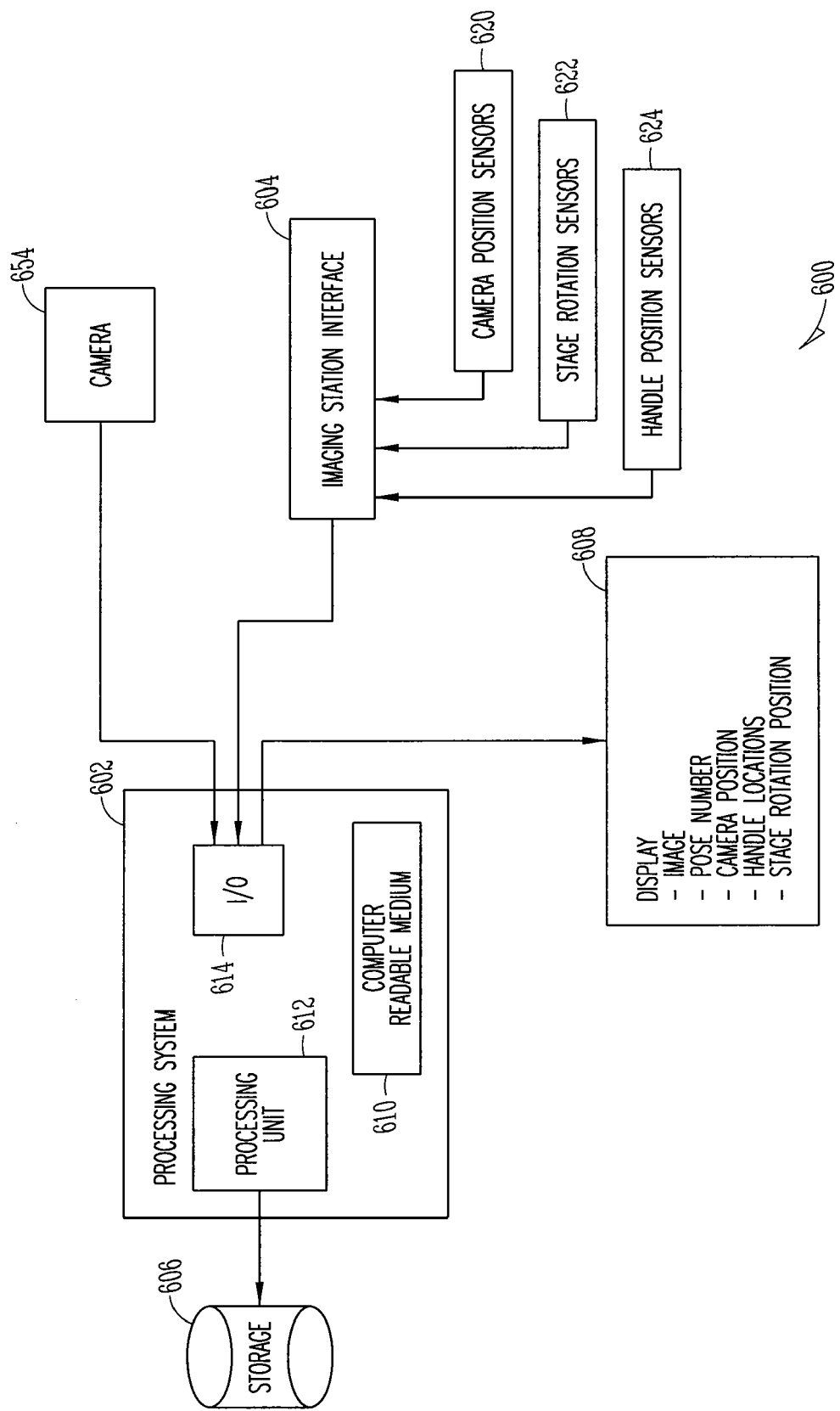
FIG. 6 illustrates an imaging system, in accordance with some embodiments.

FIG. 6 illustrates an imaging system, in accordance with some embodiments. Imaging system 600 may be configured to capture images of body poses of a subject and store the images and associated data for each body pose. Imaging system 600 may include processing system 602, imaging station interface 604, storage element 606, display 608, and camera 654. In some embodiments, image acquisition system 600 may include imaging station 100 (FIG. 1) and camera 654 may correspond to camera 154 (FIG. 1). In accordance with these embodiments, computer-readable medium 610 may store instructions thereon in the form of software for execution by one or more processors of processing unit 612 to perform operations to configure the processing system 602 to accept and store captured images of the body poses, including positional information for the camera, the stage and the subject for each body pose.

For each body pose, processing system 602 may be configured to store data in data storage element 606, including a body pose name or description, camera settings, camera position information as indicated by camera position-indicating elements of the monostand 152 (FIG. 1), the rotational position of the stage 102, and position indications of the handles 106A-D (FIG. 3) that are grasped by the subject for the body pose. A position indication for the foot platform 107 (FIG. 3) may also be stored for body poses that use a foot platform.

In some embodiments, image acquisition system 600 may include camera position sensors 620 on the monostand 152 to electronically sense and provide camera positional information to the processing system 602, handle position sensors 624 to electronically sense and provide handle position information to the processing system 602, and/or stage rotation sensors 622 to electronically sense and provide a rotational position of the stage 102 (FIG. 3) to the processing system 602. The processing system 602 may be configured to display this data on display 608 for an operator.

In these embodiments, the imaging system 600 may include imaging station interface 604 to provide an interface between position sensors 620, 622 and 624 and an input-output (I/O) 614 of processing system 602. In some embodiments, processing system 602 may be a general purpose computer. In some of these embodiments, camera 654 may be coupled to the processing system 602 through I/O 614 to provide captured images of the body poses.

In some other embodiments, the imaging system 600 may include servos, motors and/or hydraulic components configured to physically position the camera 654 and monostand 152, rotate the stage 102, position the handles 106A-106D, and/or position the foot platform 107 for each body pose.

Although imaging system 600 is illustrated as having several separate functional elements, one or more of the functional elements may be combined and may be implemented by combinations of software-configured elements, such as processing elements including digital signal processors (DSPs), and/or other hardware elements. For example, some elements may comprise one or more microprocessors, DSPs, application specific integrated circuits (ASICs), and combinations of various hardware and logic circuitry for performing at least the functions described herein. In some embodiments, the functional elements of imaging system 600 may refer to one or more processes operating on one or more processing elements.

Figure 7A:
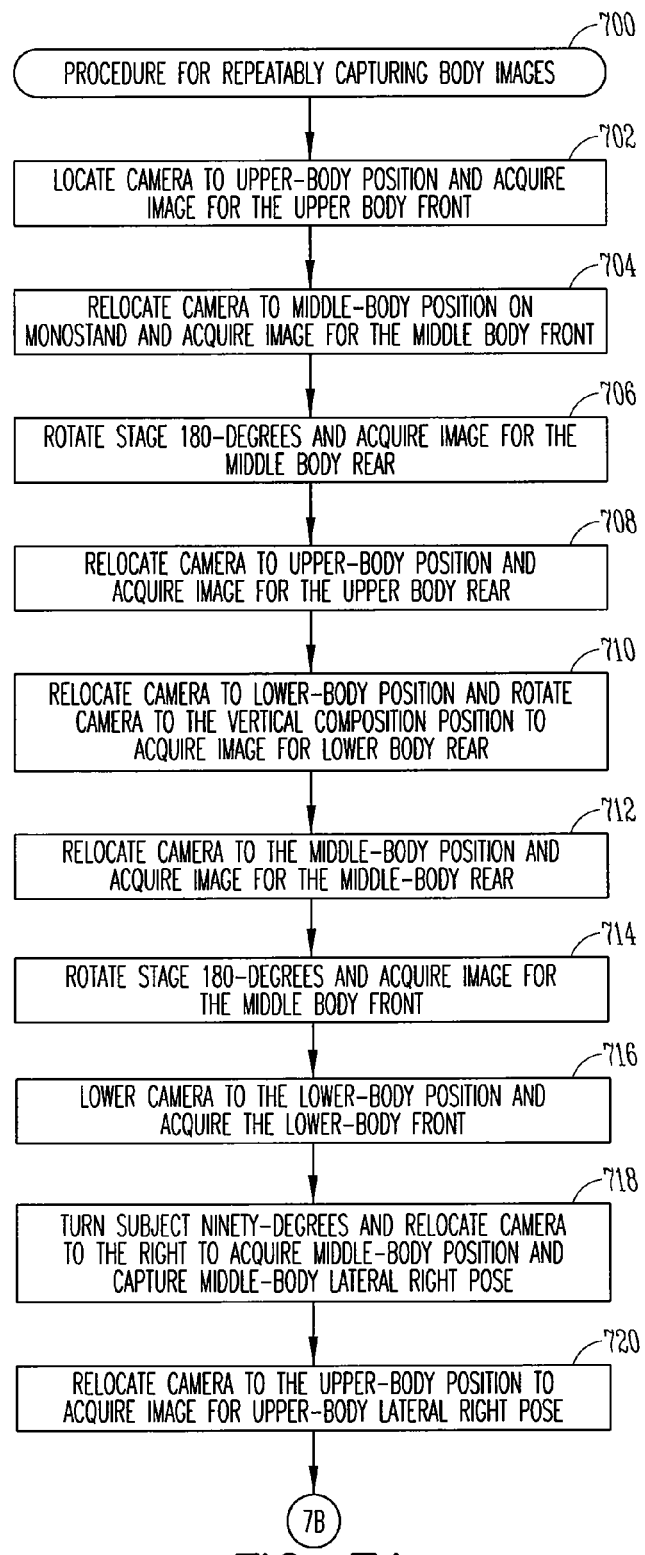
FIGS. 7A and 7B are a procedure for repeatably capturing images of body poses, in accordance with some embodiments.
Figure 7B:
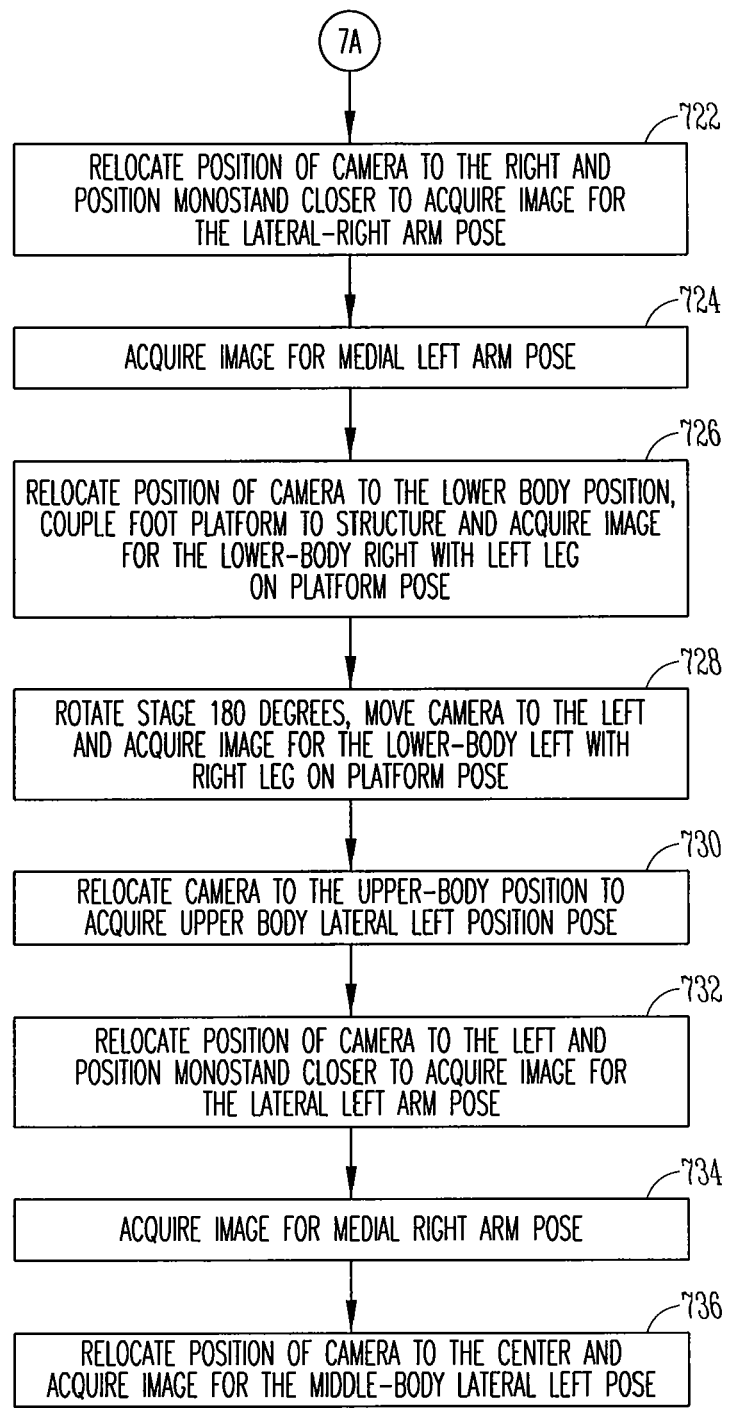

FIGS. 7A and 7B are a procedure for repeatably capturing images of body poses in accordance with some embodiments. Procedure 700 may be performed to repeatably capture a set of body images at initial and one or more subsequent times and may be performed using an imaging station, such as imaging station 100 (FIG. 1). In some embodiments, an imaging system, such as imaging system 600 (FIG. 6) may be used.

In operation 702, an image corresponding to body pose 401 (FIG. 4) is acquired for the upper body front body pose. The camera 154 is located to an upper-body position on the monostand 152. For this body pose, the subject holds handles 106C (FIG. 3) which are adjusted to provide the hands and elbows at ninety degree angles.

In operation 704, the camera 154 is relocated to a middle-body position on the monostand 152. In operation 704, an image, corresponding to body pose 402 (FIG. 4) is acquired for the middle body front position. For this body pose, the subject holds handles 106A (FIG. 3) with both hands forming a shallow 'V' formation under both arms.

In operation 706, stage 102 is rotated 180-degrees for back-views of the subject, and the position of the camera 154 is not changed from the middle-body position on the monostand 152. In operation 706, an image corresponding to body pose 403 (FIG. 4) is acquired for the middle body back position. For this body pose, the subject holds handles 106A (FIG. 3).

In operation 708, the camera 154 is relocated to the upper-body position on the monostand 152. In operation 708, an image corresponding to body pose 404 (FIG. 4) is acquired for the upper body rear position. For this body pose, the subject holds handles 106C (FIG. 3)

In operation 710, the camera 154 is relocated to the lower-body position on the monostand 152 and is rotated ninety-degrees to the vertical composition position. In operation 710, an image corresponding to body pose 405 (FIG. 4) is acquired for the lower body rear position. For this body pose, the subject continues to hold handles 106C (FIG. 3) and the subject's feet may be positioned in a predetermined set of the feet-position indicators 109.

In operation 712, the camera 154 is relocated to the middle-body position on the monostand 152 and remains in the vertical composition position. In operation 712, an image corresponding to body pose 406 (FIG. 4) is acquired for the middle body rear position. For this body pose, the subject continues to hold handles 106C (FIG. 3).

In operation 714, stage 102 is rotated 180-degrees for front-views of the subject and the position of the camera 154 is not changed from the middle-body position on the monostand 152. In operation 714, an image corresponding to body pose 407 (FIG. 4) is acquired for the middle body front position. For this body pose, the subject continues to hold handles 106C (FIG. 3).

In operation 716, the camera 154 is lowered to the lower-body position on the monostand 152 and remains in the vertical composition position. In operation 716, an image corresponding to body pose 408 (FIG. 4) is acquired for the lower body front position. For this body pose, the subject continues to hold handles 106C (FIG. 3) and the subject's feet may be positioned in a predetermined set of the feet-position indicators 109.

In operation 718, subject turns ninety-degrees for lateral right-views of the subject and the position of the camera 154 is relocated to the middle-body position on the monostand 152. In operation 718, an image corresponding to body pose 409 (FIG. 4) is acquired for the middle body-lateral right. For this body pose, the subject holds handles 106D (FIG. 3) with both hands.

In operation 720, position of the camera 154 is relocated to the upper-body position on the monostand 152. In operation 720, an image corresponding to body pose 410 (FIG. 4) is acquired for the upper body-lateral right. For this body pose, the subject holds handles 106B (FIG. 3) with both hands forming a ninety-degree angle.

In operation 722, the position of the camera 154 is relocated to the right on the monostand 152 and the monostand 152 is positioned closer to the subject. In operation 722, an image corresponding to body pose 411 (FIG. 4) is acquired for the lateral-right arm body pose. For this body pose, the subject grasps handle 106B (FIG. 3) with the right arm and drops the left arm to image the right arm.

In operation 724, the position of the camera 154 is unchanged. In operation 724, an image corresponding to body pose 412 (FIG. 4) is acquired for the medial-left arm body pose. For this body pose, the subject grasps handle 106B (FIG. 3) with the left arm and drops the right arm to image the left arm.

In operation 726, the position of the camera 154 is relocated to the lower body position and foot platform 107 (FIG. 3) may be inserted into or coupled to structure 104 (FIG. 3). In operation 726, an image corresponding to body pose 413 (FIG. 4) is acquired for the lower-body right body pose. For this body pose, the subject places the left foot on foot platform 107 (FIG. 3) to view the outer leg and inner thigh. For this body pose, the subject may hold handles 106D (FIG. 3). The subject's left foot may be positioned in one of the feet-position indicators 109.

In operation 728, stage 102 is rotated 180-degrees for left-views of the subject and the position of the camera 154 is moved to the left side. In operation 728, an image corresponding to body pose 414 (FIG. 4) is acquired for the lower-body left body pose. For this body pose, the subject places the right foot on foot platform 107 (FIG. 3) to view the outer leg and inner thigh. For this body pose, the subject may hold handles 106D (FIG. 3). The subject's left foot may be positioned in one of the feet-position indicators 109.

In operation 730, the position of the camera 154 is relocated to the upper-body position on the monostand 152 for lateral left-views of the subject. In operation 730, an image corresponding to body pose 415 (FIG. 4) is acquired for the upper body-lateral left. For this body pose, the subject holds handles 106B (FIG. 3) with both hands forming a ninety-degree angle with arms and mid-body.

In operation 732, the position of the camera 154 is relocated to the left on the monostand 152 and the monostand 152 is positioned closer to the subject. In operation 732, an image corresponding to body pose 416 (FIG. 4) is acquired for the lateral-left arm body pose. For this body pose, the subject grasps handle 106B (FIG. 3) with the left arm and drops the right arm to image the left arm.

In operation 734, the position of the camera 154 is unchanged. In operation 734, an image corresponding to body pose 417 (FIG. 4) is acquired for the medial-right arm body pose. For this body pose, the subject grasps handle 106B (FIG. 3) with the right arm and drops the left arm to image the right arm.

In operation 736, the position of the camera 154 is relocated to the center on the monostand 152. In operation 736, an image corresponding to body pose 418 (FIG. 4) is acquired for the middle-body lateral left body pose. For this body pose, the subject holds handles 106D (FIG. 3) with both hands showing the under-arm area.

Figure 8:
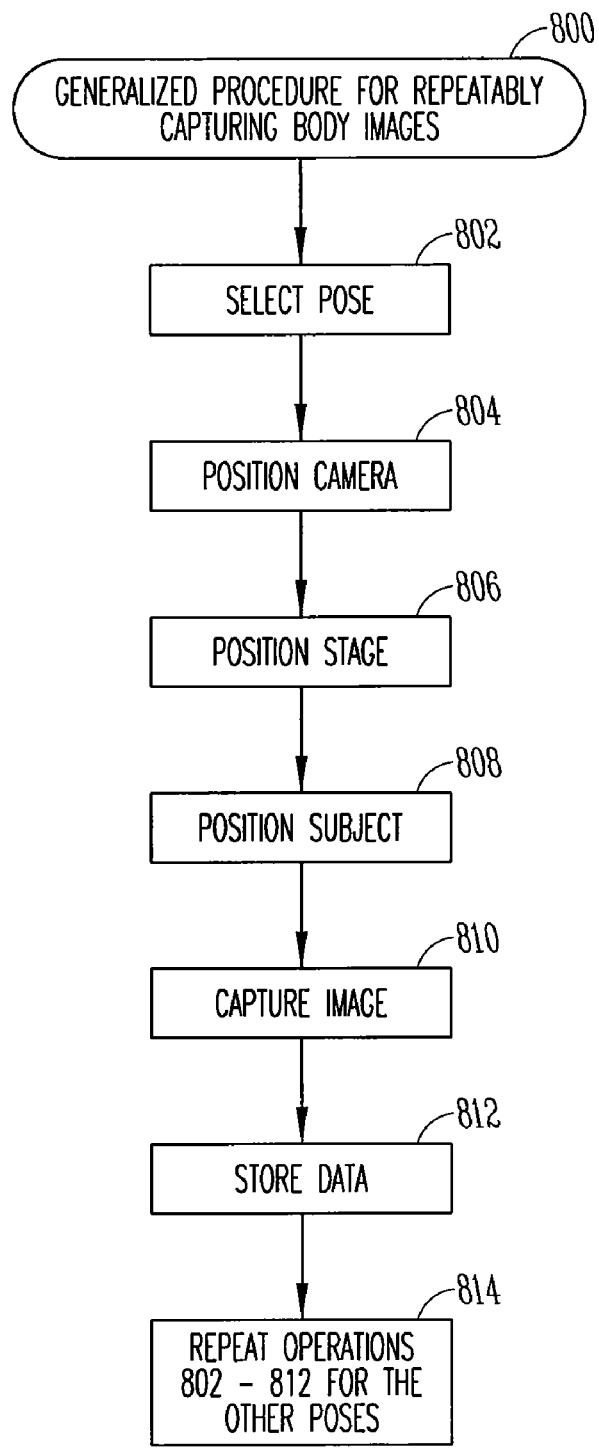
FIG. 8 is a more generalized procedure for repeatably capturing images of body poses, in accordance with some embodiments.

FIG. 8 is a more generalized procedure for repeatably capturing images of body poses, in accordance with some embodiments. Procedure 800 may be performed to repeatably capture a set of body images at an initial time and one or more subsequent times and may be performed using an imaging station, such as imaging station 100 (FIG. 1). In some embodiments, an imaging system, such as imaging system 600 (FIG. 6) may be used.

In operation 802, a body pose is selected. An initial body pose, such as body pose 401, of a sequence of body poses may be selected.

In operation 804, the camera 154 is positioned for the selected body pose. In some situations, the camera's positions on the monostand 152 may be changed (up-down or left-right) and/or the monostand 152 may be positioned either further or closer to the stage depending on the selected body pose. For some body poses, the camera 154 may also be rotated ninety-degrees.

In operation 806, the stage 102 is positioned for the selected body pose. In some situations, the stage 102 may need to be rotated to a predetermined one of the ninety-degree positions for the selected body pose. When the stage 102 does not need to be rotated, the rotational position of the stage 102 may be verified for the selected body pose.

In operation 808, the subject is positioned on the stage 102 and one or more of handles 106 associated with the selected body pose are grasped. For some body poses, the subject's foot is placed on foot platform 107.

In operation 810, the camera 154 settings may be verified and the image is captured for the selected body pose.

In operation 812, data for the selected body pose may be stored. In some embodiments, imaging system 600 may be used to store the image data as well as positional information, as discussed above.

In operation 814, operations 802-812 are repeated for each body pose of the set. The sequence of body poses may be predetermined as discussed above. It should be noted that it may not be necessary to reposition the camera, reposition the stage, or reposition the subject for each pose and accordingly, one or more of steps 804, 806 and 808 may not be performed each time operations 802-812 are repeated depending on the sequence of body poses that is selected.

In some alternate embodiments, an imaging system is provided having one or more non-rotatable stages and one or more corresponding monostands, such as the monostand 152 (FIG. 1). Rather than the stage rotating, in these embodiments, four imaging stations may be provided, each with a monostand, in which the stage for each imaging station is provided in one of the four ninety-degree positions. In this way, each imaging station may be configured to capture the body poses for one side of the subject. The subject may progress from one imaging station to the next imaging station to allow the entire set of body poses 400 (FIG. 4) to be acquired. In these embodiments, an additional one or more imaging stations may be provided to capture the images of the hands, feet, head and shoulders.

In some embodiments, a plurality of cameras may be positioned on stage 102 to capture a plurality of images simultaneously. In some of these embodiments, three-dimensional (3D) images of the body may be constructed. Black and white images may be used for alignment and tracking of skin features, while color images may be used to add color to the black and white images.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. An imaging station for repeatable alignment of photographic images for a set of body poses, the imaging station comprising:
    a stage having a structure to support sets of handles for positioning of a subject's hands for at least some of the body poses;
    the sets of handles, wherein each handle is associated with a handle-position indicator to indicate a position of the associated handle;
    a foot platform associated with a foot platform position indicator, the foot position indicator to indicate a position of the foot platform, and the foot platform to support a subject's foot for at least some of the body poses, wherein a height of the foot platform is adjustable; and
    a monostand for placement of a camera for capturing photograph images of the subject, the monostand configured to allow the camera to be repeatably positioned with respect to the stage for each body pose to allow for alignment and comparison of skin-features in corresponding photographic images taken at different times,
    wherein the handle-position indicators and the foot platform position indicator are used to repeatably position the handles for sets of body poses taken at different times,
    wherein for each body pose a predetermined one or more handles are grasped by the subject, and
    wherein a predetermined background color is provided behind the imaging station to allow for separation of body pixels from background pixels in the captured photograph images.

2. The imaging station of claim 1 wherein the monostand includes:
    a forward-backward camera position-indicating element to indicate a distance from the camera to the stage;
    a left-right camera position-indicating element to indicate a left-right position of the camera; and
    an up-down camera position-indicating element to indicate an up-down position of the camera.

3. The imaging station of claim 1 wherein the stage is a rotatable stage that is configured to rotate to one of a plurality of ninety-degree positions with respect to the monostand.

4. The imaging station of claim 1 wherein the monostand comprises a light source and a fiber-optic cable, wherein the fiber-optic cable is coupled to the camera to project light through a lens for use in focusing and framing the photographic images.

5. The imaging station of claim 1 wherein the imaging station is configured to allow data for each body pose to be recorded, the data for each body pose to include:
a body pose name or description;
camera settings;
camera position information as indicated by camera position-indicating elements of the monostand;
a position of the stage;
position indications of the handles that are grasped; and
for body poses that use a foot platform, a position indication for the foot platform.

6. The imaging station of claim 2 wherein the monostand includes a support element to support the camera,
wherein the left-right position-indicating element is provided on the support element,
wherein the support element is configured to slide horizontally to allow the left-right position of the camera to be changed, and
wherein the camera is configured to be rotated ninety degrees.

7. The imaging station of claim 3 wherein the rotatable stage includes:
a mat with feet-position indicators thereon for placement of the subject's feet.

8. The imaging station of claim 3 wherein the rotatable stage comprises:
wheels to allow rotation of the structure; and
a circular track to allow rotation of the rotatable stage around a central axis.

9. The imaging station of claim 5 wherein when a subsequent set of photographic images for the subject are to be captured after an initial set of photographic images are captured, the imaging station is configurable to allow precise repeat capturing of a photographic image for each of the body poses based on the data recorded for each body pose.

10. A method for repeatably capturing photographic images of body poses comprising:
positioning a camera in a predetermined camera position using a monostand;
positioning a rotatable stage in a predetermined rotational position;
positioning one or more handles in a predetermined position using a handle-position indicator;
adjusting a height of a foot platform using a foot platform position indicator;
positioning a subject on the rotatable stage in a predetermined subject position, the predetermined subject position including the subject either grasping the one or more handles or placing a foot on the foot platform; and
providing a predetermined background color behind the subject opposite the camera to allow for separation of body pixels from background pixels in a photograph image,
wherein the photographic image is captured for each body pose of a plurality of body poses after the camera, the subject and the rotatable stage are positioned, and
wherein the monostand is configured to allow the camera to be repeatably positioned with respect to the stage for each body pose to allow for alignment and comparison of skin-features in corresponding photographic images taken at different times.

11. The method of claim 10 wherein each body pose is associated with:
the predetermined camera position on the monostand;
the predetermined subject position for the subject including positions of the handles as indicated by handle-position indicators for the handles that are grasped; and
the predetermined rotational position of the rotatable stage.

12. The method of claim 11 further comprising selecting a predetermined sequence to capture the photographic images for a set of the body poses, the sequence being selected either for increased subject comfort or for reduced camera movement.

13. The method of claim 11 further comprising:
repeating the positioning steps to capture photographic images of body poses at a subsequent time by positioning the rotatable stage, the subject and the camera in accordance with data recorded for each body pose at a prior time, the data including:
a body pose name or description;
camera settings;
camera position information as indicated by camera position-indicating elements of the monostand;
a rotational position of the rotatable stage;
position indications of the handles that are grasped; and
for body poses that use a foot platform, a position indication for the foot platform.

14. The method of claim 11 wherein the rotatable stage includes a structure to support sets of the handles for positioning of the subject's hands for at least some of the body poses; and
wherein the monostand includes:
a forward-backward camera position-indicating element to indicate a distance from the camera to the rotatable stage;
a left-right camera position-indicating element to indicate a left-right position of the camera; and
an up-down camera position-indicating element to indicate an up-down position of the camera.

15. The method of claim 14 wherein the method includes, for at least some of the body poses:
rotating the rotatable stage to one of a plurality of ninety-degree positions with respect to the monostand for a body pose;
moving either the camera or the monostand to a predetermined position based on the positions indicated on the camera position-indicating elements; and
positioning the subject on the rotatable stage to grasp one or more of the handles.

16. An imaging system to capture photographic images of body poses of a subject and associated data for each body pose, the system comprising:
an imaging station comprising a rotatable stage to support the subject and a monostand to support a camera, and
a non-transitory computer-readable medium that stores instructions for execution by one or more processors to perform operations to configure a processing system to accept and store captured photographic images of the body poses including positional information for the camera, the rotatable stage and the subject for each body pose,
wherein the rotatable stage includes a structure to support sets of handles for positioning of hands of the subject for at least some of the body poses,
wherein the monostand is configurable for placement of the camera for capturing photographic images of the subject to allow the camera to be repeatably positioned with respect to the rotatable stage for each body pose to allow for alignment and comparison of skin-features in corresponding photographic images taken at different times, and
wherein for each body pose, the processing system is configured to store data including:

a body pose name or description;
camera settings;
camera position information as indicated by camera position-indicating elements of the monostand;
a rotational position of the rotatable stage;
position indications of the handles that are grasped by the subject for the body pose; and
for body poses that use a foot platform, a position indication for the foot platform, wherein the position indication for the foot platform includes a height of the foot platform, and
wherein a predetermined background color is provided behind the imaging station to allow for separation of body pixels from background pixels in the captured photograph images.

17. The imaging system of claim 16 further comprising:
camera position sensors on the monostand to electronically provide camera positional information to the processing system;
handle position sensors to electronically provide handle positional information to the processing system; and
stage rotation sensors to electronically provide a rotational position of the rotatable stage to the processing system.

18. An imaging station for capturing photographic images for a set of body poses, the imaging station comprising:
a rotatable stage having a structure to support sets of handles for positioning of a subject's hands for at least some of the body poses, wherein the rotatable stage includes
the set of handles each handle of the set of handles associated with a handle position indicator; and
a foot platform having an adjustable height, the foot platform associated with a foot platform position indicator; and
monostand for placement of a camera for capturing photographic images of the subject, the monostand configured to allow the camera to be repeatably positioned with respect to the rotatable stage for each body pose to allow for alignment and comparison of skin-features in corresponding photographic images taken at different times,
wherein the rotatable stage is configured to rotate to one of a plurality of ninety-degree positions with respect to the monostand,
wherein the monostand includes a plurality of camera position-indicating elements to indicate three-dimensional positions of the camera with respect to stage,
wherein the handle-position indicators and the foot platform position indicator are used to repeatably position the handles for sets of body poses taken at different times,
wherein for each body pose a predetermined one or more handles are grasped by the subject, and
wherein a predetermined background color is provided behind the subject opposite the camera to allow for separation of body pixels from background pixels in the captured photograph images.

19. The imaging station of claim 18, wherein the rotatable stage includes:
a mat with feet-position indicators thereon for placement of the subject's feet;
wheels to allow rotation of the structure; and
a circular track to allow rotation of the rotatable stage around a central axis.

* * * * *

UNITED STATES PATENT AND TRADEMARK OFFICE
CERTIFICATE OF CORRECTION

| | | |
|---|---|---|
| PATENT NO. | : 8,351,770 B2 | Page 1 of 1 |
| APPLICATION NO. | : 12/404864 | |
| DATED | : January 8, 2013 | |
| INVENTOR(S) | : DePaula et al. | |

It is certified that error appears in the above-identified patent and that said Letters Patent is hereby corrected as shown below:

On the title page, in column 2, under "Other Publications", line 1, delete "C," and insert --C.,--, therefor On title page 2, in column 1, under "Other Publications", line 2, delete "detectionof" and insert --detection of--, therefor On title page 2, in column 1, under "Other Publications", line 5, delete "Internationai" and insert --International--, therefor In the Specification In column 5, line 4, after "Arm", insert --body pose--, therefor In the Claims In column 13, line 28, in Claim 18, after "includes", insert --:--, therefor In column 13, line 29, in Claim 18, after "handles", insert --,--, therefor In column 14, line 1, in Claim 18, before "monostand", insert --a--, therefor Signed and Sealed this
Twenty-ninth Day of September, 2015

Michelle K. Lee
*Director of the United States Patent and Trademark Office*